(12) United States Patent
Glover et al.

(10) Patent No.: US 7,691,399 B2
(45) Date of Patent: Apr. 6, 2010

(54) COSMETIC COMPOSITIONS WITH LONG LASTING SKIN MOISTURIZING PROPERTIES

(75) Inventors: David A. Glover, Palos Park, IL (US); Natalya Y. Gurman, Mt. Prospect, IL (US)

(73) Assignee: Alberto Culver Company, Melrose Park, IL (US)

( * ) Notice: Subject to any disclaimer, the term of this patent is extended or adjusted under 35 U.S.C. 154(b) by 717 days.

(21) Appl. No.: 10/771,028

(22) Filed: Feb. 3, 2004

(65) Prior Publication Data
US 2005/0169879 A1 Aug. 4, 2005

(51) Int. Cl.
*A61K 8/00* (2006.01)

(52) U.S. Cl. ...................................... 424/401

(58) Field of Classification Search .......... None
See application file for complete search history.

(56) References Cited

U.S. PATENT DOCUMENTS

| 4,610,874 | A | * | 9/1986 | Matravers | ................ | 424/70.13 |
| 2003/0133957 | A1 | * | 7/2003 | Amalric et al. | ............. | 424/401 |
| 2004/0170587 | A1 | * | 9/2004 | Vondruska | ............... | 424/70.12 |

FOREIGN PATENT DOCUMENTS

| EP | 0780116 | A1 | 6/1997 |
| EP | 1430867 | A | 6/2004 |
| GB | 1295108 | A | 11/1972 |
| GB | 1307644 | A | 2/1973 |
| JP | 61229812 | A | 10/1986 |
| WO | WO 03/032943 | A1 | 4/2003 |
| WO | WO 2004/026259 | A2 | 4/2004 |

OTHER PUBLICATIONS

Amazon.com ST.IVES 24 Hour Moisture Advanced Therapy Lotion for Extra Dry Skin. . . Amazon.com, URL<www.amazon.com/gp/product/B0000DBNEW/002-6434883-7339224?v=glance &n=3760901> accessed Apr. 7, 2006 pp. 1-4.*

Ashberry et al. Colloid & Surface Phenomena, Apr. 9, 2002, URL ,www.eng.buffalo.edu/Courses/ce457_527/ce457_pro/g9doc2.htm> pp. 1-23.*

St. Ives; 24 Hour Moisture Advanced Therapy Lotion; Oct. 8, 2003 URL ,http://http://www.uspto.gov/web/offices/pac/dapp/opla/preognotice/moreinfoamdprac.htm.archive.org/http://www.uspto.gov/web/offices/pac/dapp/opla/preognotice/moreinfoamdprac.htm/20031008021821/http://www.stives.com/products/show_product.cfm?pid=52> 1 page.*

Household Products Database; Herbal Essence Ultra Rich Moisturizing Body Wash; [Online] URL< http://hpd.nlm.nih.gov/cgi-bin/household/brands?tbl=brands&id=16003383> pp. 1-3.*

* cited by examiner

*Primary Examiner*—Patricia Leith
(74) *Attorney, Agent, or Firm*—Leydig, Voit & Mayer, Ltd.

(57) ABSTRACT

Cosmetic composition and related method for treating skin preferably comprising an olive oil-based compound, a quaternary ammonium salt, sodium pyrrolidone carboxylic acid, and an emulsifier.

18 Claims, No Drawings

COSMETIC COMPOSITIONS WITH LONG LASTING SKIN MOISTURIZING PROPERTIES

TECHNICAL FIELD OF THE INVENTION

The present invention relates to topical cosmetic compositions that exhibit long lasting moisturizing properties, as well as to methods of using these compositions.

BACKGROUND OF THE INVENTION

Topical cosmetic compositions are commonly formulated to provide one or more desirable properties. One of these properties, common to many cosmetic compositions, is skin moisturization.

Moisturization is typically imparted to these compositions by using one or a combination of two well-known technologies: including a humectant, such as glycerin or sorbitol, to hydrate the skin and prevent water loss, and/or forming a barrier against moisture loss by including substances such as petrolatum or heavy oils.

While these technologies are effective, each has drawbacks. For example, humectants can be sticky and tacky, must be used in relatively high concentrations to be effective, work only on the surface of the skin, and are easily washed off. Barrier-forming ingredients, on the other hand, are marginally effective, feel greasy and oily, and, like humectants, wear off a short time after application onto the skin. Among other drawbacks, neither technology provides for relatively long-term skin moisturization.

Other moisturizers are designed to work at the cellular level by rebuilding or preventing damage to the skin's natural barrier layer. Central to this barrier layer is the outermost layer of the epidermis, referred to as the horny cell layer (i.e., the stratum corneum). This layer provides primary protection against skin damage due to ultraviolet light and other environmental influences, and also acts to prevent excessive dryness.

The horny cell layer, however, is continually worn down due to contact with the environment and, therefore, must be constantly renewed. While this renewal occurs naturally, renewal can be interrupted by various endogenous and exogenous factors. When interrupted, the barrier layer's ability to function properly is impeded because dead, dull skin cells undesirably do not slough off regularly, and the natural lipids in the horny cell layer, such as ceramides, cholesterol, esters and the like, cannot properly control the amount of moisture evaporating from the epidermis.

Illustrative of these exogenous factors is ultraviolet light. Ultraviolet light can initiate a chain reaction that transforms lipids in the horny cell layer into free radical species. The free radical species, once formed, attack other lipids in the horny cell layer, thereby forming more free radical species which, in turn, results in the damage of more lipids. As more lipids are damaged, the skin's natural moisture barrier loses its ability to effectively regulate moisture retention in the skin. The damaged natural lipid layer permits more moisture to escape from the skin than is absorbed into the skin, resulting in dry skin.

Moisturizers acting at the cellular level are designed to penetrate the surface of the skin and repair the natural lipid layer, e.g., by facilitating the ability of dead, dull skin cells to slough off more regularly and/or by acting as free radical scavengers to prevent the free radicals from continuing the deleterious chain reaction.

Despite the availability of cosmetic moisturizing compositions, a need exists for topical cosmetic compositions that provide, among other beneficial properties, enhanced skin moisturization over an extended period of time without sacrificing after-feel, e.g., the skin is not rendered oily and greasy.

BRIEF SUMMARY OF THE INVENTION

The present invention meets the foregoing and other needs by providing, in a first aspect, a topical cosmetic composition an olive oil-based compound and a quaternary ammonium salt. In a related and preferred aspect, the aforementioned inventive composition further comprises sodium pyrrolidone carboxylic acid (NaPCA) and, in a more preferred aspect, an emulsifier.

Other aspects of the invention include methods of using the inventive compositions for enhancing moisture retention in the skin, or for inhibiting the rate of moisture loss from the skin, comprising topically applying at least one of the inventive compositions onto skin.

It has been found that the inventive compositions exhibit improved skin moisturizing properties over longer periods of time, and better after-feel, relative to existing compositions.

The present invention may be best understood with reference to the following detailed description of the preferred embodiments.

DETAILED DESCRIPTION OF THE INVENTION

The present invention provides, in one aspect, a topical cosmetic composition comprising, at least, a quaternary ammonium salt, and an olive oil-based compound.

In a related aspect, the inventive composition further comprises NaPCA and, in a further aspect, an emulsifier.

It was surprisingly found that the inventive compositions exhibit unexpected improvement in moisturization properties, over relatively long periods of time, and further provided enhanced after-feel. The improvement in the aforesaid properties was unexpected in view of the properties of each individual component used in the inventive compositions.

The inventive compositions include, at least, two components: a quaternary ammonium salt and an olive oil-based compound.

The quaternary ammonium salt used in the present invention may be any salt that assists in providing the composition with the benefits described herein, but desirably comprises an amino acid or protein derivative of a quaternary ammonium salt. Preferably cationic, this component is believed to assist in providing the composition with its long lasting moisturization properties. In theory, this component penetrates the skin, unlike humectants such as glycerin, and works at the cellular level to hydrate and bind moisture therein.

In more preferred embodiments, the quaternary ammonium salt comprises lysine hydroxypropyltrimonium chloride. Flexiquat™, which further contains keratin amino acids and gelatin, is a preferred source of this component.

The precise amount of quaternary ammonium salt in the present invention may vary in accordance with the desired properties of the composition in which it is included, but is desirably present in an amount of from about 0.000001% to about 5% by weight of the composition. More preferably, this salt is present in an amount of from about 0.00001% to about 2% by weight of the composition, and most preferably from about 0.00005% to about 1% by weight of the composition, e.g., from about 0.000002-4%, from about 0.000004-3%, from about 0.00002-1.5%, from about 0.00004-1.2%, or from about 0.00006-0.9% by weight of the composition.

The olive oil-based compound used in the present invention may be selected from a group well known to those of ordinary skill in the art. These compounds may also assist in providing the composition into which they are incorporated with the benefits described herein. Illustrative of suitable olive oil-based compounds include olive oil polyethyleneglycol (PEG) esters (including derivatives thereof, such as, but not limited to, olive oil PEG-6 esters, olive oil PEG-7 esters, olive oil PEG-10 esters), olive oil extract, olive husk extract, olive leaf extract, olive oil unsaponifiables, olive oil fatty acid derivatives, olivamidopropyl (and derivatives thereof, such as, but not limited to, olivamidopropyl dimethylamine, olivamidopropyl dimethylamine lactate, and olivamidopropyl betaine), olivamide DEA, and olivamidopropalkonium chloride.

In one preferred embodiment, the olive oil-based compound comprises an olive oil. Olive oil, also known as *Olea europaea* oil or *Oleum olivae*, is a fixed oil obtained from the ripe fruit of the *Olea europaea*, containing glycerides of oleic acid, palmitic acid, linoleic acid, stearic acid, and arachidic acid. It is a yellow to light green liquid having a slight olive odor. It is slightly soluble in alcohol, insoluble in water, and miscible in ether, chloroform, and carbon disulfide.

In another preferred embodiment, the olive oil-based compound comprises an olive oil PEG derivative, such as an olive oil PEG ester. An olive oil PEG ester is a nonionic, complex mixture formed from the transesterification of olive oil and polyethylene glycol (PEG). These esters are believed to function in the inventive compositions as a humectant, able to bind moisture better than other humectants such as glycerin, while being substantially free of the tacky feel associated with many humectants.

The amount of olive-oil based compound in the present invention may vary, depending on the degree to which the properties provided by this component are desired in the inventive composition, but is desirably present in an amount of from about 0.001% to about 15% by weight of the composition. Preferably, this compound is present in an amount of from about 0.01% to about 10% by weight of the composition, and more preferably from about 0.1% to about 5% by weight of the composition, e.g., from about 0.002-13%, from about 0.004-11%, from about 0.02-8%, from about 0.04-6%, or from about 0.2-4% by weight of the composition.

Advantageously, sodium PCA (NaPCA), also known as sodium pyroglutamate or sodium DL-2-pyrrolidone-5-carboxylate, is included in the inventive compositions. Its empirical formula is $C_5H_7NO_3 \cdot Na$, and is provided as a colorless and odorless liquid with a molecular weight of 151.1. This component assists in enhancing the feel of the composition, imparting a pleasing moist feel to the skin, increasing skin softness and elasticity. It is believed that this component plays a role in maintaining a relatively constant moisture level in the skin.

When included in an inventive composition, the amount of NaPCA may vary, depending on the properties desired in the composition to which NaPCA is included, but this component is desirably included in an amount of from about 0.0001% to about 5% by weight of the composition. Preferably, this component is included in an amount of from about 0.0005% to about 3% by weight of the composition, and more preferably from about 0.001% to about 1% by weight of the composition, e.g., from about 0.0002-4%, from about 0.0004-4%, from about 0.006-2%, from about 0.004-1%, or from about 0.02-0.5% by weight of the composition.

In a further aspect of the invention, an emulsifier may be included in the compositions. While emulsifiers are well known in the art, those that are suitable for topical use on skin are most desirable. Examples of emulsifiers that may be used in the present invention can be found in the Handbook of Cosmetic and Personal Care Additives, 2d Edition (2002), published by Synapse Information Resources, which is incorporated herein by reference in its entirety. Preferred emulsifiers suitable for use in the present invention include isoceteth-20, dicetyl phosphate, ceteth-10-phosphate, sodium stearate, stearic acid, cetearyl alcohol, stearamidopropyldimethylamine, behentrimonium methosulfate, sodium methyl cocoyl taurate, cetearyl glucoside, sodium methyl oleoyl taurate, sodium lauryl sulfate and the like, alone or in combination, with cetearyl glucoside being most preferred.

Preferred emulsifiers, and particularly the glucosides, are believed to assist in enhancing the retention of water within the skin. For example, cetearyl glucosides, is thought to strengthen the lipid structure within the skin, establishing a barrier to moisture loss.

The amount of emulsifier that may be included in the compositions of the present invention may vary, depending on the degree to which the properties provided by this component are desired in the inventive composition, but, if present, is desirably in an amount of from about 0.001% to about 10% by weight of the composition. Preferably, the emulsifier may be present from about 0.01% to about 7% by weight of the composition, and more preferably from about 0.1% to about 5% by weight of the composition, e.g., from about 0.002-8%, from about 0.004-6%, from about 0.02-5%, from about 0.04-4%, or from about 0.2-3% by weight of the composition.

It is further preferred that, if present, the various components used in providing the present invention be included in particular weight ratios. For example, there should be a greater amount by weight of the olive oil-based component included in the composition than of the NaPCA component, desirably from about a 10:1 to about a 2:1 weight ratio; a greater amount of emulsifier than the olive oil-based component, desirably from about a 5:1 to greater than a 1:1 weight ratio; and a lesser amount of the quaternary ammonium salt component relative to the olive oil-based component, desirably from about 1:100 to about 1:1000 weight ratio.

When the four components mentioned previously are used, the components are preferably included in certain weight ratios. For example, it is preferred that the weight ratio of the olive oil-based compound to the quaternary ammonium salt in the composition ranges from about 5000:1 to about 7000:1; the weight ratio of the emulsifier to the quaternary ammonium salt in the composition ranges from about 11,000:1 to about 9000:1; and the weight ratio of the sodium PCA to the quaternary ammonium salt in the composition ranges from about 400:1 to about 600:1.

The beneficial effects provided by the composition and methods of the invention are useful for a number of different cosmetic applications. For example, the inventive compositions of the present invention may be included in a variety of topical products, e.g., facial moisturizers, eye creams and lotions, hand lotions, body lotions, and the like. These compositions can be formulated into any suitable form, e.g., a gel, a lotion, a cream, a solution, or the like, as will be appreciated by the ordinarily skilled artisan.

In some aspects of the present invention, for example, cream and lotion formulations, the composition may be provided the form of a water-in-oil emulsion or, preferably, an oil-in-water emulsion. As is well known, in a water-in-oil emulsion, the oil phase is the continuous (or external) phase, and dispersed within the oil phase is the aqueous (or internal) phase. An oil-in-water emulsion is the opposite; the aqueous phase is the continuous phase and the oil phase is dispersed within the aqueous phase. Emulsion formulations are preferred as they assist in providing uniform application of the composition onto the skin and possess good skin feel.

Even if the composition is not in the form of an emulsion, water and/or oil (other than the olive oil-based component) can be included in the composition. If water and/or oil are included, in an emulsion or otherwise, they can be included in any amount suitable to provide the desired properties in the finished composition. For example, if water is included in an emulsion or other composition (e.g., dispersion) form, it desirably may be present in an amount of from about 40% to about 95% by weight of the composition. If oil is present, it desirably may be present in an amount of from about 10% to about 95% by weight of the composition, more preferably, in an amount of from about 10% to about 50% by weight of the composition.

If present, the oil may be any of a number of components suitable for inclusion in a topical cosmetic composition. Illustrative oils, some of which may function as emollients, include silicone oils, triglyceride esters, natural oils, waxes, hydrocarbons, phospholipids, polyhydric and fatty alcohols, polyether derivatives, and the like, as well as those described in U.S. Pat. Nos. 5,980,921 and 6,042,815, or combinations thereof.

Illustrative of preferred oils are silicone oils. Silicone oils may be provided in the form of one or more volatile silicones, non-volatile silicones, and mixtures thereof. Exemplary silicone oils include, e.g., cyclomethicone, phenyl trimethicone, alkyl dimethicone, fluorinated silicones, dimethicone, and the like, or combinations thereof. It is thought that these oils assist in enhancing uniform delivery and ease in spreading of the inventive compositions.

Although not essential, the composition of the invention may also include one or more optional ingredients, such as, for example, a thickener, a preservative, an emollient, a moisturizing additive, a neutralizer, a fragrance, an antioxidant, skin conditioner or the like.

In included, any suitable thickener may be utilized in accordance with the present invention. By way of example, the thickener can be in the form of gum, cellulosics, acrylic polymers, carbomers, and the like, or combinations thereof. Especially suitable thickeners include, but are not limited to, glyceryl stearate, cetyl alcohol, carbomer, $C_{10}$-$C_{30}$ alkyl acrylate cross polymer, and the like, or combinations thereof. The thickener may be provided in any suitable amount, for example, to achieve the desired viscosity of the composition, preferably from about 300,000 to about 400,000 cps (RV, T-Bar "C," 5 RPM, 60 sec. penetration).

Preferably, the thickener is present in an amount of from about 0.01% to about 5% by weight of the composition.

The composition optionally may further include a preservative. For example, the preservative may be selected to kill bacteria that might otherwise be sustained or multiply in the composition. Preservatives suitable for this purpose are well known to those skilled in the art. In this respect, the type of preservative chosen will depend upon the components and the structure of the composition. For example, some preservatives are selected to combat microorganisms that are sustained in water, while others are selected to combat microorganisms that are sustained in oil. Illustrative of suitable preservatives include ethylparaben, propylparaben, methylparaben, EDTA or salts thereof (such as disodium EDTA), phenoxyethanol, DMDM hydantoin, and the like, or combinations thereof. The preservative may be present in any effective amount, such as an amount of from about 0.01% to about 3%, or preferably form about 0.5% to about 2%, by weight of the composition.

The composition may also include an emollient. As used herein, emollient refers to a material used for the prevention or relief of dryness, as well as for the protection of the skin. The emollient desirably may be included to complement the emollient properties of the oil mentioned previously, if the latter is present in the composition. Any suitable emollient may be included, and a wide variety of such emollients are known and may be used. Sagarin, Cosmetics, Science and Technology, 2nd Edition, Vol. 1, pp. 32-43 (1972), incorporated herein by reference, contains numerous examples of materials suitable as an emollient. By way of example, the emollient can be selected from $C_{12}$-$C_{15}$ alkyl benzoate, $C_{12}$-$C_{15}$ alkyl octanoate, caprylic triglycerides, capric triglycerides, mineral oil, cetearyl alcohol, dimethicone, cyclomethicone, shea butter, and the like, or combinations thereof. If present, the emollient may be included in any suitable amount, such as, for example, in an amount of from about 0.1% to about 10%, preferably from about 3% to about 8%, by weight of the composition.

The compositions of the present invention may also include one or more moisturizing additives. Any suitable moisturizing additive may be used. Illustrative moisturizing additives include, but are not limited to, esters, humectants, urea, glycerine, retinyl palmitate, petrolatum, gelatin, keratin amino acids, lysine hydroxypropyl trimonium chloride, propylene glycol, natural botanical extracts, such as *chamomile recutita* extract, *sambucus nigra* extract, *primula veris* extract, glycerin, *helianthus annuus* extract and the like, as well as phospholipids, silicones, occlusive agents, natural oils, barbadensis gel, and the like, or combinations thereof. If included, the moisturizing additives may be included in any suitable amount, for example, in an amount of from about 0.0001% to about 25%, preferably from about 2% to about 10%, by weight of the composition.

If it is desired to include petrolatum in the inventive compositions, it is preferred to use a cationic emulsion of petrolatum and silicone. This emulsion provides enhanced performance relative to petrolatum per se. It is believe that the relatively small size of the petrolatum particles in the emulsion permits the composition to easily penetrate the skin and form a barrier to moisture loss without the greasy feel associated with petrolatum per se.

If desired, the composition may further include one or more neutralizers, such as, for example, strong and weak bases. Any suitable neutralizer can be selected, as will be appreciated by one of ordinary skill in the art. Exemplary neutralizers suitable for use in the compositions of the present invention included sodium hydroxide, potassium hydroxide, ammonium hydroxide, diethanolamine, triethanolamine, 2-dimethylamino-2-methyl-1-propanol (DAMP), 2-aminomethyl- I propanol (aminomethyl propanol) (AMP), and the like, or combinations thereof. The neutralizer, if present, may be provided in any amount, e.g., an amount sufficient to achieve a desired pH for the composition. In this respect, the composition preferably has a pH of from about 4-9, more preferably, from about 5-8, and still more preferably from about 5.5-7. Typically, the neutralizer may be present in an amount of from about 0.01% -10% by weight of the composition.

The composition may also include a fragrance, if desired. The fragrance may be selected from those suitable for cosmetic preparations, as is well known to those skilled in the art. If included, the fragrance may be present in an amount of from about 0.01% to about 3% by weight of the composition.

An antioxidant may also be included in the compositions of the present invention, is desired. The antioxidant may be any antioxidant suitable for cosmetic preparations, as should be appreciated by one skilled in the art. Illustrative of suitable antioxidants include coenzyme Q10, vitamin C, vitamin E, superoxide dismutase (SOD), tocopheryl acetate, ascorbic acid, and the like, or combinations thereof. While the antioxidant may be included in any suitable amount, it may desirably be included in an amount of from about 0.00001% to about 5%, preferably from about 0.05% to about 1%, by weight of said composition.

The composition may further include, if desired, a skin conditioner. The skin conditioner may be suitable skin conditioner, as will be appreciated by those skilled in the art. Exemplary skin conditioners include phytantriol, panthenyl ethyl ether, primula veris extract, chamomi, sambucus nigra flower extract, panthenol, polyquaternium-51, cetyl alcohol, glycolic acid, stearyl alcohol, and the like, or combinations thereof. The skin conditioner can be included in the present inventive composition in any suitable amount, but may desirably be included in an amount of from about 0.1% to about 5% by weight of said composition.

In some embodiments, the composition may be in the form of a water-in-oil emulsion or an oil-in-water emulsion comprising an aqueous phase, which preferably is present in an amount of from about 50% to about 90% by weight of the composition; an oil phase, which preferably is present in an amount of from about 10% to about 50% by weight of the composition; an emulsifier, which preferably is present in an amount of from about 0.001% to about 20% by weight of the composition; a thickener, which preferably is present in an amount of from about 0.001% to about 5% by weight of the composition; a preservative, which preferably is present in an amount of from about 0.001% to about 3% by weight of the composition; a neutralizer, which preferably is present in an amount of from about 0.001% to about 10% by weight of the composition; a fragrance, which preferably is present in an amount of from about 0.001% to about 3% by weight of the composition; an emollient, from about 0.001% to about 10% by weight of the composition; a moisturizing additive, which preferably is present in an amount of from about 0.001% to about 20% by weight of the composition; an antioxidant, which preferably is present in an amount of from about 0.00001% to about 5% by weight of the composition; and a skin conditioner, which preferably is present in an amount of from about 0.1% to about 5% by weight of the composition.

In accordance with the present invention, upon topical application of the composition to the skin, the composition preferably imparts long-lasting moisturization to the skin as measured by a moisture index. Several analytical methods and/or devices well known to those of ordinary skill in the art may be used to measure the moisture index. One such device is the Novameter DPM 9003 (Nova Corporation, Portsmouth, N.H.).

The Novameter DPM 9003 is a dermatological laboratory instrument commonly used in the cosmetics industry. In using the DPM 9003, a remote, uniform-pressure sensor probe is employed. Readings are taken by lacing the sensor probe on the surface of the skin. The device displays DPM values (a moisture index), which represent relative values of skin characteristics based on the capacitive reactance of the skin. DPM values can be monitored and stored when the optional DPM 9900 series of software is used with a MS-DOS compatible computer.

The values of the DPM 9003 device range between a low of 90 to a high of 999. Lower values generally represent dry skin while higher values represent hydrated skin. It should be appreciated that the conversion of Novameter values into percentage increases in moisturization is well known in the cosmetic industry, and is calculated based on the readings obtained from the Novameter DPM 9003 according to the following equation: percentage increase=[(final value−initial value)/initial value]×100.

In a preferred embodiment, the moisture index of skin treated with the compositions of the present invention about 10 minutes after application is at least about 35% higher, more preferably at least about 45% higher, and most preferably at least about 50% higher, relative to untreated skin. More preferably, the moisture index of skin treated with the compositions of the present invention about 20 minutes after application is at least about 30% higher, more preferably at least about 40%, and most preferably at least about 45%, relative to untreated skin.

The present invention also provides an increase in moisturization, and other beneficial effects, to skin over relatively longer periods of time, e.g., up to 4, 8, 12 and 24 hours, without the disadvantages of existing formulations, e.g., oily or tacky feel, and the like.

The following examples further illustrate the invention but should not be construed as in any way limiting its scope.

EXAMPLE 1

This example demonstrates the skin moisturizing properties of a preferred formulation of the present invention that includes a combination of NaPCA, a emulsifier, a quaternary ammonium salt, and an olive oil-based compound.

Five samples (Sample 1A, and Comparative Samples 1B, 1C, 1D, and 1E) were prepared and evaluated. Sample 1A contained a combination of NaPCA, cetearyl glucoside, lysine hydroxypropyltrimonium chloride, and an olive oil PEG ester, in certain amounts and ratios: 1.0% cetearyl glucoside, 0.5% olive oil PEG ester, 0.1% NaPCA, 0.0001% lysine hydroxypropyltrimonium chloride, and 98.3999% deionized water. Comparative Sample 1B comprised 0.1% NaPCA and 99.9% deionized water. Comparative Sample 1C comprised 0.0001% lysine hydroxypropyltrimonium chloride and 99.9999% deionized water. Comparative Sample 1D comprised 1% cetearyl glucoside and 99% deionized water. Finally, Comparative Sample 1E comprised 0.5% olive oil PEG ester and 99.5% deionized water. Each sample was prepared as an aqueous dispersion.

The testing protocol used in this example is as follows. Two human subjects were chosen. Baseline moisturization scores obtained using a Novameter 9003 at the epidermal sites prior to application of the Comparative Samples (Initial Value). Each assigned sample was then applied to the epidermal sites of the subjects. At about 10 and 20 minutes after application of each Comparative Sample composition, skin moisturization measurements were again taken using the Novameter DPM 9003. The results of the skin moisturizing effect of each Comparative Sample are shown in Table 1. From the data gathered, percent changes in skin moisturization were calculated using the following equation: Percentage Increase=[(Final Value−Initial Value)/Initial Value]×100.

TABLE 1

| | Percent Change in Skin Moisturization | | | |
|---|---|---|---|---|
| | Subject No. 1 | | Subject No. 2 | |
| Sample | 10 min. | 20 min. | 10 min. | 20 min. |
| Control (Untreated Skin) | −1.56% | −1.56% | −14.04% | −7.02% |
| Sample 1A | 62.75% | 58.82% | 64.62% | 52.31% |
| Comparative Sample 1B | −5.08% | 0.00% | −8.47% | −13.56% |
| Comparative Sample 1C | −1.79% | 1.79% | −12.70% | −14.29% |
| Comparative Sample 1D | 10.53% | 7.02% | −1.75% | 0.00% |
| Comparative Sample 1E | 14.29% | 1.79% | 0.00% | −3.28% |

The results demonstrate an improvement in immediate skin moisturizing properties provided by a preferred embodiment of the present invention, represented by Sample 1A. Sample IA exhibited over 60% maximum increase in skin moisturization after about ten minutes, and over a 50% maximum increase after 20 minutes. The maximum increase in skin moisturization exhibited by each of the components of Sample 1A alone (in the Comparative Samples), whether taken alone or combined, were well under that provided when using Sample 1A.

The results suggest a surprising and unexpected synergistic moisturization effect is provided by the compositions of the present invention, as the effect could not be predicted based upon the performance of each component alone.

EXAMPLE 2

The following is an example of a preferred composition of the present invention. The components in the composition are identified below in Table 2, with the quantities shown in the "Wt. %" column representing the weight percent of each composition component as a percentage of the total composition weight.

TABLE 2

| Description | Wt. % |
|---|---|
| Water | 78.4145 |
| Olive Oil PEG-7 Esters | 0.6 |
| Sodium PCA | 0.05 |
| Gelatin/Keratin Amino Acids/Lysine Hydroxypropyl Trimonium Chloride | 0.0001 |
| Preservative | 0.55 |
| Thickener | 2.25 |
| Moisturizing Additive | 6.5 |
| Emollient | 6.2 |
| Emulsifier | 5.0 |
| Neutralizer | 0.35 |
| Antioxidant | 0.0004 |
| Fragrance | 0.075 |
| Skin Conditioner | 0.01 |

The composition, an oil-in-water emulsion, was prepared using methods well known to those skilled in the art.

All references, including publications, patent applications, and patents cited herein are hereby incorporated by reference to the same extent as if each reference were individually and specifically indicated to be incorporated by reference and were set forth in its entirety herein.

The use of the terms "a," "an," "the," and similar referents in the context of describing the invention are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise described. No language in the specification should be construed as indicating that any non-essential element is essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context.

What is claimed is:

1. A cosmetic composition comprising
   from 0.001% to 15% by weight of an olive oil polyethylene glycol (PEG) ester,
   from 0.000001% to 5% by weight of lysine hydroxypropyltrimonium chloride,
   from 0.0001% to 5% by weight of sodium pyroglutamate (sodium PCA)
   from 0.001% to 10% by weight of cetearyl glucoside, and water,
   wherein the weight ratio of the olive oil PEG ester to the lysine hydroxypropyltrimonium chloride in the composition is from 5000:1 to 7000:1.

2. The composition of claim 1, wherein the composition is in the form of an emulsion.

3. The composition of claim 1, wherein
   the weight ratio of the cetearyl glucoside to the lysine hydroxypropyltrimonium chloride in the composition is from 11,000:1 to 9000:1; and
   the weight ratio of the sodium PCA to the lysine hydroxypropyltrimonium chloride in the composition is from 400:1 to 600:1.

4. The composition of claim 1, wherein the olive oil PEG ester is present in an amount of from 0.01% to 10% by weight of the composition; the lysine hydroxypropyltrimonium chloride is present in an amount of from 0.00001% to 2% by weight of the composition; the sodium PCA is present in an amount of from 0.0005% to 3% by weight of the composition; and the cetearyl glucoside is present in an amount of from 0.01% to 7% by weight of the composition.

5. The composition of claim 4, wherein the olive oil PEG ester is present in an amount of from 0.1% to 5% by weight of the composition; the lysine hydroxypropyltrimonium chloride is present in an amount of from 0.00005% to 1% by weight of the composition; the sodium PCA is present in an amount of from 0.001% to 1% by weight of the composition;

and the cetearyl glucoside is present in an amount of from 0.1% to 5% by weight of the composition.

6. The composition of claim 1, further comprising at least one of the following components:
   (a) a thickener;
   (b) a preservative:
   (c) a neutralizer;
   (d) an emollient;
   (e) a fragrance;
   (f) a moisturizing additive;
   (g) an antioxidant; and
   (h) a skin conditioner.

7. The composition of claim 6, further comprising at least two of components (a)-(h).

8. The composition of claim 7, further comprising at least components (a), (d) and (f).

9. The composition of claim 8, further comprising:
   a thickener present in an amount of from 0.001% to 5% by weight of the composition;
   a preservative present in an amount of from 0.001% to 3% by weight of the composition;
   a neutralizer present in an amount of from 0.001% to 10% by weight of the composition;
   an emollient present in an amount of from 0.001% to 10% by weight of the composition;
   a fragrance present in an amount of from 0.001% to 3% by weight of the composition;
   a moisturizing additive present in an amount of from 0.001% to 20% by weight of the composition;
   an antioxidant present in an amount of from 0.00001% to 5% by weight of the composition;
   a skin conditioner present in an amount of from 0.1% to 5% by weight of the composition; and
   water present in an amount of from 40% to 95% by weight of the composition.

10. The composition of claim 1, wherein the composition is in the form a cream, a lotion, a solution, an ointment, or a gel.

11. The composition of claim 10, wherein the composition is an emulsion.

12. The composition of claim 1, wherein the olive oil PEG ester is an olive oil PEG-7 ester.

13. A method of enhancing moisture retention in the skin comprising topically applying onto the skin a moisture-retaining effective amount of a composition comprising
   from 00.01% to 15% by weight of an olive oil PEG ester,
   from 0.000001% to 5% weight of lysine hydroxypropyltrimonium chloride,
   from 0.0001% 5% by weight of sodium PCA,
   from 0.001% 10% by weight of cetearyl glucoside, and
   water,
   wherein the weight ratio of the olive oil PEG ester to the lysine hydroxypropyltrimonium chloride in the composition is from 5000:1 to 7000:1.

14. The method of claim 13, wherein
   the weight ratio of the cetearyl glucoside to the lysine hydroxypropyltrimonium chloride in the composition is from 11,000:1 to 9000:1; and
   the weight ratio of the sodium PCA to the lysine hydroxypropyltrimonium chloride in the composition is from 400:1 to 600:1.

15. The method of claim 13, wherein the olive oil PEG ester in an olive oil PEG-7 ester.

16. A method for inhibiting the rate of moisture loss from the skin comprising topically applying onto the skin a moisture-loss inhibiting effective amount of a composition comprising
   from 0.001% to 15% by weight of an olive oil PEG ester,
   from 0.000001% to 5% by weight of lysine hydroxypropyltrimonium chloride,
   from 0.0001% to 5% by weight of sodium PCA,
   from 0.001% to 10% by weight of cetearyl glucoside, and
   water,
   wherein the weight ratio of the olive oil PEG ester to the lysine hydroxypropyltrimonium chloride in the composition is from 5000:1 to 7000:1.

17. The method of claim 16, wherein
   the weight ratio of the cetearyl glucoside to the lysine hydroxypropyltrimonium chloride in the composition is from 11,000:1 to 9000:1;
   the weight ratio of the sodium PCA to the lysine hydroxypropyltrimonium chloride in the composition is from 400:1 to 600:1.

18. The method of claim 16, wherein the olive oil PEG ester is an olive oil PEG-7 ester.

* * * * *

UNITED STATES PATENT AND TRADEMARK OFFICE
CERTIFICATE OF CORRECTION

PATENT NO. : 7,691,399 B2  Page 1 of 1
APPLICATION NO. : 10/771028
DATED : April 6, 2010
INVENTOR(S) : David A. Glover et al.

It is certified that error appears in the above-identified patent and that said Letters Patent is hereby corrected as shown below:

Col. 10; Claim 1, line 39, "(sodium PCA)" should read --(sodium PCA),--

Col. 12; Claim 13, lines 1-5, "from 00.01% to 15% by weight of an olive oil PEG ester, from 0.000001% to 5% weight of lysine hydroxypropyltrimonium chloride, from 0.0001% 5% by weight of sodium PCA, from 0.001% 10% by weight of cetearyl glucoside, and" should read --from 0.001% to 15% by weight of an olive oil PEG ester, from 0.000001% to 5% by weight of lysine hydroxypropyltrimonium chloride, from 0.0001% to 5% by weight of sodium PCA, from 0.001% to 10% by weight of cetearyl glucoside, and--

Col. 12; Claim 17, line 37, "from 11,000:1 to 9000:1;" should read --from 11,000:1 to 9000:1; and--

Signed and Sealed this

Twenty-third Day of November, 2010

David J. Kappos
*Director of the United States Patent and Trademark Office*